United States Patent [19]
Furumoto et al.

[11] Patent Number: 5,624,435
[45] Date of Patent: Apr. 29, 1997

[54] ULTRA-LONG FLASHLAMP-EXCITED PULSE DYE LASER FOR THERAPY AND METHOD THEREFOR

[75] Inventors: Horace W. Furumoto, Wellesley; Harry L. Ceccon, Boston, both of Mass.; Antonio G. Rizzo, Nashua, N.H.

[73] Assignee: Cynosure, Inc., Bedford, Mass.

[21] Appl. No.: 461,952

[22] Filed: Jun. 5, 1995

[51] Int. Cl.$^6$ ................................................. A61M 5/06
[52] U.S. Cl. ................................. 606/10; 606/3; 606/9; 606/13
[58] Field of Search ................... 606/2, 3–18; 372/6, 372/25–28

[56] References Cited

U.S. PATENT DOCUMENTS

| | | | |
|---|---|---|---|
| 3,766,488 | 10/1973 | Kohn | 372/53 |
| 4,292,601 | 9/1981 | Aldag et al. | 331/94.5 |
| 4,829,262 | 5/1989 | Furumoto | 606/2 |
| 4,862,886 | 9/1989 | Clarke et al. | 606/7 |
| 4,977,571 | 12/1990 | Furumoto et al. | |
| 5,057,099 | 10/1991 | Rink | |
| 5,066,293 | 11/1991 | Furumoto | 606/9 |
| 5,092,865 | 3/1992 | Rink | 606/12 |
| 5,109,387 | 4/1992 | Garden et al. | |
| 5,180,378 | 1/1993 | Kung et al. | 606/2 |
| 5,287,380 | 2/1994 | Hsia | |
| 5,387,211 | 2/1995 | Saadatmanesh et al. | 606/10 |

FOREIGN PATENT DOCUMENTS

95/04393   2/1995   WIPO.

OTHER PUBLICATIONS

"A Simple Reliable Waveguide Dye Laser for Ophthalmological Applications" by Burlamacchi et al; Rev of Sci Instrum; vol. 46; No. 3; pp. 281–283, Mar. 1975.

Anderson, R.R., et al., "Microvasculature Can Be Selectively Damaged Using Dye Lasers: A Basic Theory and Experimental Evidence in Human Skin," *Lasers in Surgery and Medicine*, 1:263–276 (1981).

Boiteux, M., et al., "A Transverse Flow Repetitive Dye Laser," *Applied Optics*, 9, 514 (1970).

Anderson, R.R., et al., "Selective Photothermolysis: Precise Microsurgery by Selective Absorption of Pulsed Radiation," *Science*, 220:524–527, Apr. (1983).

"Flashlamp Excited Dye Lasers," *Candela Corporation, 96 South Avenue, Natick, Massachusetts* 01760, (1979) Commercial Brochure.

Sierra, R., "Flashlamp-Excited Dye Lasers Achieve New Performance Levels," *Laser Focus/Electro–Optics* 2394(4):77–91 (Apr. 1988).

*Primary Examiner*—David M. Shay
*Attorney, Agent, or Firm*—Hamilton, Brook, Smith & Reynolds, P.C.

[57] ABSTRACT

A flashlamp-excited dye laser generating light pulses for therapy has a circulator which circulates a gain media through a dye cell. A controller coordinates operation by triggering flashlamps to excite the laser gain media while the circulator is circulating the gain media. This operation enables the generation of laser light pulses with a duration of at least one millisecond. If the flow velocity of dye solution is great enough such that the new solution enters the resonant cavity before the solutions in the cavity are substantially spent, ultra-long pulses with high fluences are possible. Specifically, longer pulses of up to 50 msec can be achieved with energies of up to 50 Joules. These energies enable reasonable spot sizes, which makes the invention relevant to dermal therapy, for example.

3 Claims, 5 Drawing Sheets

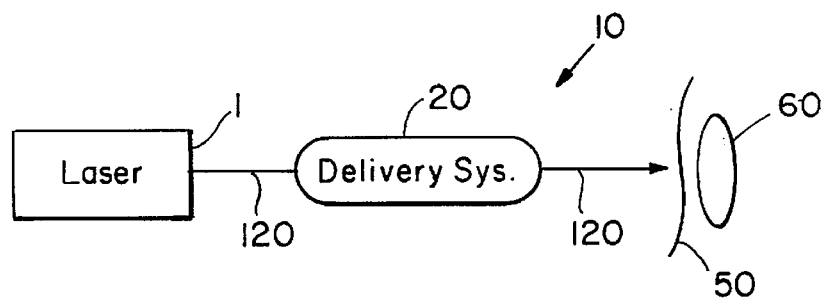
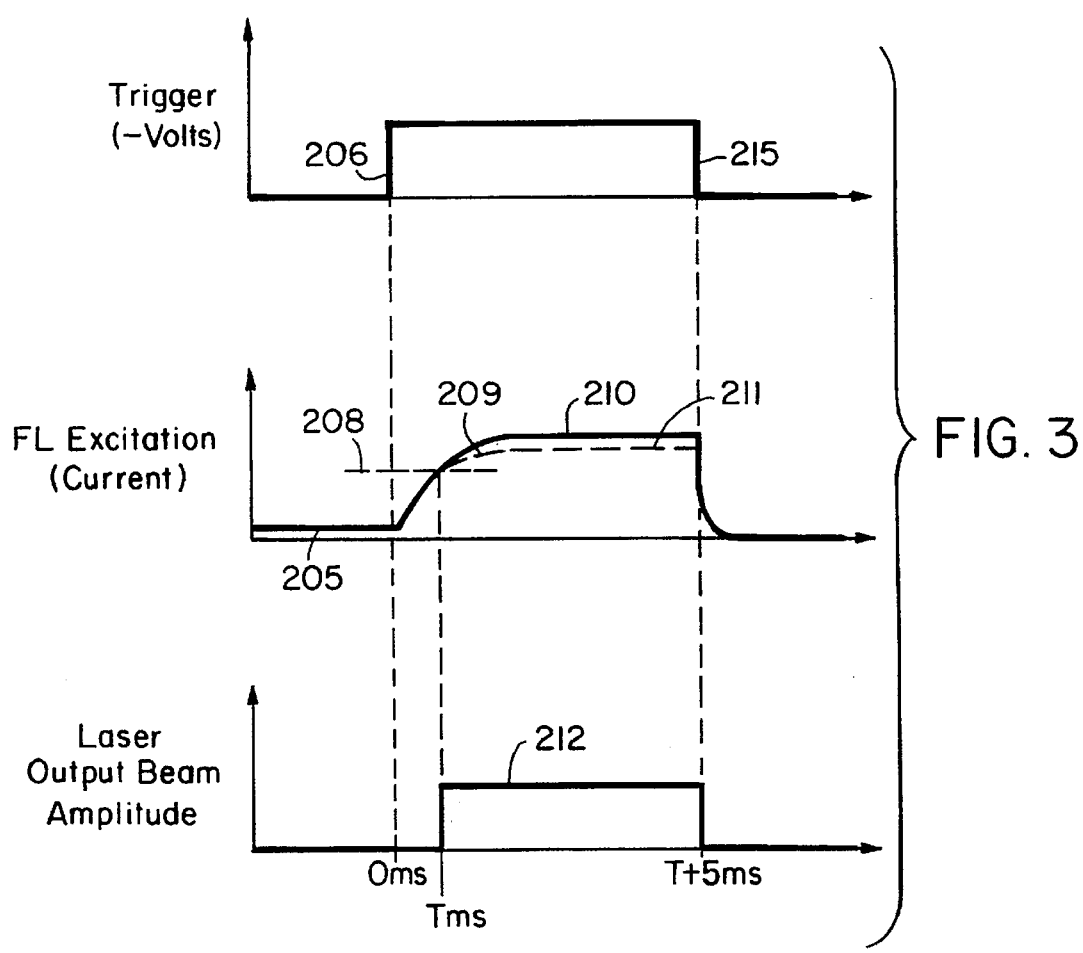

ULTRA-LONG FLASHLAMP-EXCITED PULSE DYE LASER FOR THERAPY AND METHOD THEREFOR

BACKGROUND OF THE INVENTION

Vascular lesions, comprising enlarged or ectatic blood vessels, pigmented lesions, and tattoos have been successfully treated with lasers for many years. In the process called selective photothermolysis, the targeted structure, the lesion tissue or tattoo pigment particles, and the surrounding tissue are collectively irradiated with laser light. The wavelength or color of this laser light, however, is chosen so that its energy is preferentially absorbed by the target. Localized heating of the target resulting from the preferential absorption leads to its destruction.

Most commonly in the context of vascular lesions, such as portwine stains for example, hemoglobin of red blood cells within the ectatic blood vessels serves as the laser light absorber, i.e., the chromophore. These cells absorb the energy of the laser light and transfer this energy to the surrounding vessel as heat. If this occurs quickly and with enough energy, the vessel reaches a temperature to denature the constituents within the boundary of the vessel. The fluence, Joules per square centimeter, to reach the denaturation of a vessel and the contents is calculated to be that necessary to raise the temperature of the targeted volume within the vessel to about 70° C. before a significant portion of the absorbed laser energy can diffuse out of the vessel. The fluence must, however, be limited so that the tissue surrounding the vessel is not also denatured.

As suggested, simply selecting the necessary fluence is not enough. The intensity and pulse duration of the laser light must also be optimized for selectivity by both minimizing diffusion into the surrounding tissue during the pulse while avoiding localized vaporization. Boiling and vaporization lead to mechanical, rather than chemical, damage-which can increase injury and hemorrhage in the tissues that surround the lesion. This constraint suggests that for the fluence necessary to denature the contents of the vessel, the pulse duration should be long and at a low intensity to avoid vaporization. It must also not be too long because of thermal diffusivity. Energy from the laser light pulse must be deposited before heat dissipates into the tissue surrounding the vessel. The situation becomes more complex if the chromophore is the blood cell hemoglobin within the lesion blood vessels, since the vessels are an order of magnitude larger than the blood cells. Radiation must be added at low intensities so as to not vaporize the small cells, yet long enough to heat the blood vessels by thermal diffusion to the point of denaturation and then terminated before tissue surrounding the blood vessels is damaged.

Conventionally, flashlamp-excited dye lasers have been used as the laser light source. These lasers have the high spectral brightness required for selective photothermolysis and can be tuned to colors for which preferential absorption occur. For example, colors in the range of 577 to 585 nm match the alpha absorption band of hemoglobin and thus are absorbed well by the red blood cells in the blood vessels. The absorption of melanin, the principal pigment in the skin, is poor in this range, yielding the necessary selectivity.

The implementation of flashlamp-excited dye lasers presents problems in the pulse length obtainable by this type of laser. Theory dictates that the length of the light pulse should be on the order of the thermal relaxation time of the ectatic vessels. Ectatic vessels of greater than 30 microns in diameter are characteristic of cutaneous vascular lesions. These large vessel have relaxation times of 0.5 msec and require pulse durations of this length. Commercially available flashlamp-excited dye lasers generally have maximum pulse lengths that are shorter than 0.5 msec. As a result, selective photothermolysis treatment of ectatic vessels larger than 30 microns currently relies on higher than optimum irradiance to compensate for the pulse duration limitations. This leads to temporary hyperpigmentation, viz., purpura.

Attempts have been made to increase the pulse durations of flashlamp-excited dye lasers. The Light Amplifier disclosed in U.S. Pat. Nos. 4,829,262 and 5,066,293 was conceived by the present inventor to mitigate laser quenching from thermal effects. The design centered on developing a spatially non-coherent laser. Basically, the optics at each end of the dye cell are designed to return substantially all of the light emanating from the end aperture back through the dye cell and reflect off the dye cell walls. Specific resonating and coherent modes are not favored. The optics mix the rays and thoroughly homogenize the beam. Thus, the effects from thermal distortions induced by the flashlamp are mitigated since resonator modes are not required for lasing action to occur. The invention of this patent does not generate a light that can be concentrated to the degree obtainable by classic laser configurations. But, the large depth of field and tightly focused beams that coherent radiation provides are not necessary for many medical applications. In treating vascular lesions, focussed spots a few millimeters in diameter are adequate. It is often convenient to use fiber optic delivery systems and all that is necessary is to be able to focus the energy from the long pulse dye laser into a fiber approximately one millimeter in diameter.

Newer devices to treat vascular lesions are once again built according to the typical laser paradigm, i.e. lasers that generate spatially coherent light. It turns out that with optimization, these lasers generate pulse lengths that can equal or exceed those achievable by the design producing spatially incoherent radiation described above. Interestingly, dye choice has a large impact on pulse duration. Reduction in dye degradation by improving longevity through dye chemistry has enabled pulse durations approaching 1.0 msec in commercially available devices.

SUMMARY OF THE INVENTION

It has been observed that the premature cessation of the lasing is caused primarily by the degradation of the dye solutions. As a result, improved dye solutions can yield some increases in pulse duration. Dye degradation, however, can not be totally eliminated and other steps must be taken if pulse durations of 5 msec and greater and having the fluences for medical procedures are to be achieved.

The present invention is based in part upon the realization that if, in a flashlamp-excited dye laser, the dye solution is replaced during lasing with the proper speed, the extended pulses and fluences required for medical procedures are possible in a single laser device. This operation is achieved by triggering the flashlamp while a dye solution is being circulated through the resonant cavity of the laser. If the flow velocity of dye solution is great enough such that the new solution enters the cavity before the solutions in the cavity are substantially spent, ultra-long pulses with high fluences are possible. Specifically, longer pulses of up to 50 msec can be achieved with energies of up to 50 Joules. These high energies enable treatment with reasonable spot sizes, which makes the invention relevant to dermal therapy.

According to one aspect, the invention features a flashlamp-excited dye laser generating light pulses at a color and pulse duration required for selective photothermolysis. This laser comprises a cell containing a laser gain media located in a cavity. Dye solutions are typical examples of such gain media. At least one flashlamp is provided to excite the gain media contained in the cell. A circulator is used to circulate the gain media through the cell. Finally, a controller coordinates operation by triggering the flashlamp to excite the laser gain media while the circulator is circulating the gain media through the cell. This generates the laser light pulse with a duration of at least one millisecond. Or, another way, the flashlamp excites the laser gain media for a duration of the time in which noncirculated laser gain media in the cell would be exhausted and would quench the output laser light. But since the media is circulated, the pulse duration is extended.

For some applications, the duration of the output laser light pulse is preferably at least five milliseconds. Generally the energy of the pulse is less than twenty Joules. Further, the laser light pulses are generated with a repetition rate of about 1 Hertz, and usually less than three times a second.

In specific embodiments, the circulator replaces gain media in the dye cell with new gain media at least once during a duration of the output laser light pulse, and preferably more than once. This operation ensures that the laser output will not be quenched by accumulation of exhausted dye solutions, for example. The gain media flow through the dye cell can be transverse to the laser axis, or it can be longitudinal, parallel to the axis. Preferably, if the longitudinal configurations are implemented, a plurality of media input ports should be provided along the cell. A plurality of media output ports are also probably necessary to allow flow out of the cell. The dye cell segments between the adjacent inlet and outlet ports is ideally short so that the residence time of the flowing gain media through the dye cell segment is several times shorter than the laser pulse duration.

In the transverse flow embodiment, the gain media flows between two parallel or nearly parallel transparent cell walls, which allows the excitation light to enter the dye cell. The transparent cell wall are long in the direction of the flashlamps and laser resonator axis and shorter in the direction of the flow. The gain media flows perpendicular to the long axis of the window and is contained within the flashlamp windows and within another set of windows which allow the laser light to reflect between mirrors that comprise the laser resonator.

According to another aspect, the invention can also be characterized in the context of a method of operation for a flashlamp-excited dye laser. Such a method comprises exciting the dye solution in the resonant cavity with a flashlamp and then generating a laser light output pulse from the resonant cavity with the excited dye solution. The excitation at least partially exhausts the dye solution. To counteract this effect, some of the at least partially exhausted dye solution is replaced in the resonant cavity with new dye solution during the duration of the laser light output pulse and the new dye solution excited in the resonant cavity. This extends the duration of the laser light output pulse beyond a time at which the original dye solution in the resonant cavity cell would be exhausted and would quench the output laser light pulse if the original dye solution were never replaced.

In general, according to still another aspect, the invention features a pumping device driver for a dye laser, for example. This driver comprises a sensor for detecting an amplitude of a laser light output pulse from the laser. A circuit is then used to regulate power supplied to a pumping device, which is exciting the gain media of the laser, in response to the amplitude detected by the sensor.

In specific embodiments, the pumping device is a flashlamp and the laser is a dye laser.

The above and other features of the invention including various novel details of construction and combinations of parts, and other advantages, will now be more particularly described with reference to the accompanying drawings and pointed out in the claims. It will be understood that the particular method and device embodying the invention is shown by way of illustration and not as a limitation of the invention. The principles and features of this invention may be employed in various and numerous embodiments without the departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 schematically shows a selective photothermolysis treatment system of the invention;

FIG. 3 is a timing diagram showing the relationship between the trigger signal from the controller 160, the flashlamp driving current, and the laser pulse amplitude for one pulse of the dye laser 1;

DETAILED DESCRIPTION OF THE PREFERRED EMBODIMENTS

Figure 2:
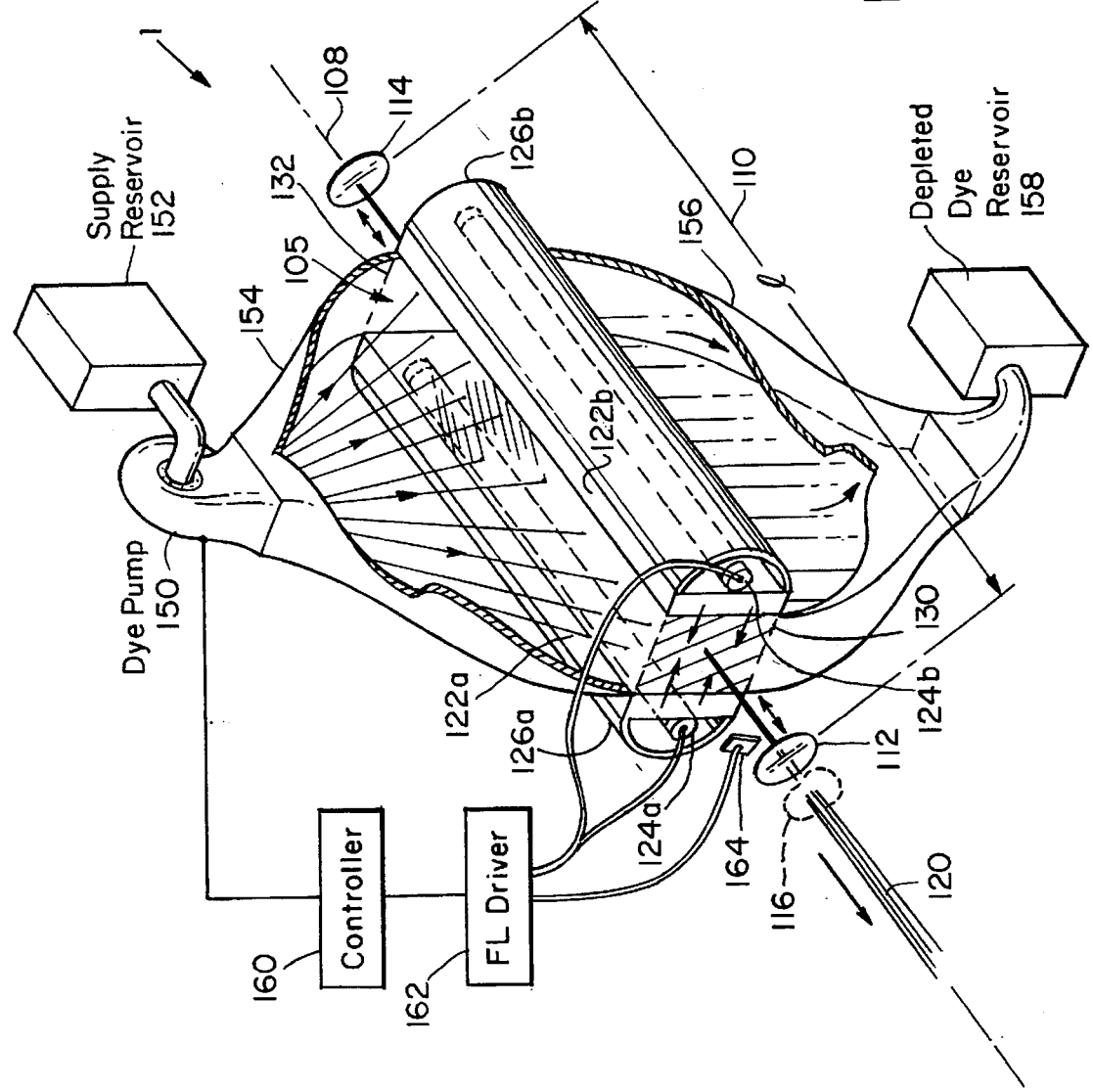
FIG. 2 is a schematic perspective view of a first embodiment of the flashlamp-excited pulse dye laser 1 of the present invention.

Turning now to the drawings, FIG. 1 shows a selective photothermolysis treatment system 10, Which has been constructed according to the principles of the present invention. A flashlamp-excited pulse dye laser 1 for the system 10 generates an output laser light pulse 120. The output laser light pulse 120 is coupled into a medical delivery system 20, such as a single optical fiber, and transported to the skin 50 or other tissue of a patient. The output laser light pulse 120 achieves substantial penetration to treat a vascular lesion 60. This lesion 60 could be of one of many different types such as portwine stain birthmarks, hemangiomas, telangiectasia, idiopathic vulvoddynia, and leg veins. Further, it could also be vessels in simple wrinkles, caused by age or sun exposure, blood vessels in scar tissue, or hair follicles.

The pulse durations of the output laser light pulse 120 are matched to the thermal relaxation time of the targeted ectatic vessels. Generally, this requires durations greater than 0.2 msec. For vessels of 30 microns in diameter and larger, as are present in portwine stains of adult patients, the duration should ideally exceed 0.5 msec, whereas pulse durations of 1 msec to 10 msec should be selected when the vessels are larger than 100 microns.

FIG. 2 is a schematic diagram illustrating the flashlamp-excited pulse dye laser 1 in more detail. As is generally common among most such lasers, a dye cell 105 for containing a liquid laser gain media, specifically a dye solution, extends longitudinally along a center axis 108 of the laser 1. A front window 130 and a rear window 132 define the longitudinal extents of the dye cell 105. Both windows 130 and 132 are transparent. The dye cell 105 is located in a resonant cavity 110, the ends of which are defined by a first mirror 112 and a second mirror 114. Usually, the cavity does not support only single longitudinal mode or single frequency. While the second mirror 114 is fully reflective, the first mirror 112 is partially reflective and partially transmissive, defining an output aperture 116. As a result, a portion of the light generated in the resonant cavity 110 passes through this first mirror 112 as the output beam 120 of the laser 1.

The dye solution in the dye cell 105 is optically pumped by flashlamps 124a and 124b. Exterior to a light-transmissive left side wall 122a of the dye cell 105 is a left flashlamp 124b. A right flashlamp 124a is on an exterior side of a right side wall 122b, which is also transmissive to light. These flashlamps 124a, 124b generate broadband light that excites the dye solution contained in the dye cell 105. This results in the stimulated emission of light from the excited dye solution. Right and left reflectors 126a and 126b surround the respective flashlamps 124a and 124b to maximize the light injected into the dye cell 105. These reflectors can be elliptical or diffuse.

According to the invention, the flashlamps 124a and 124b used in the present invention preferably have higher pulse energies than typically found in short pulse dye lasers. During the generation of an output laser light pulse of 5 msecs, the total pumping energy injected into the dye solution by the flashlamps is approximately 2000 Joules.

A dye circulator functions to circulate dye solution through the dye cell 105 while that dye solution is being excited by the flashlamps 124a, 124b. This operation enables a flashlamp-excited pulse dye laser 1 to extend the duration of the output laser light pulse 120 beyond that would be obtainable in a dye laser in which the degraded dye was not replaced during the laser pulse. For example, in a conventional laser, the degradation of the dye during the output laser light pulse would quench the lasing action within usually about 0.5 msec. In the present invention, the duration of the output laser light pulse 120 is increased beyond this quench time of the conventional laser by essentially injecting new dye into the resonant cavity to replace degraded dye that absorbs laser light and quench laser action and thus increase the pulses duration. In the embodiment shown, this circulator includes a dye pump 150 which receives new dye solution from a supply reservoir 152. The dye is pumped into a supply manifold 154 (shown here in phantom), which distributes the dye solution flow along the longitudinal axis 108 of the dye laser 1. The dye solution flows through the dye cell 105, and thus the resonant cavity 110, in a direction transverse to the axis 108 of the laser 1. A collection manifold 156 (in phantom) collects the dye solution after it has passed through the dye cell 105 and directs it to a depleted dye reservoir 158.

A separate supply reservoir 152 and depleted dye reservoir 158 are not strictly necessary. Recirculation and filtration systems are possible. U.S. patent application Ser. No. 08/165,331, filed on Dec. 10, 1993, entitled Method and Apparatus for Replenishing Dye Solution in a Dye Laser, which is incorporated herein by this reference, is directed a system in which by-products from the lasing process are filtered out and the dye solution reused.

A controller 160 coordinates the operation of the dye pump 150 and the triggering of the flashlamps 124a and 124b to achieve extended pulse durations of the output laser light 120 by replacing exhausted dye solution in the dye cell 105 during the laser pulses. Specifically, the controller 160 first establishes a steady state flow of dye solution through the dye cell 105 by activating the dye pump 150. When the dye solution is flowing through the dye cell 105, the controller 160 then sends a trigger signal to a flashlamp driver 162. The trigger signal defines the pulse durations and causes the flashlamp driver 162 to supply a driving current to the flashlamps 124a and 124b. Light from the flashlamps excites the dye solution to lase and produce the output laser light 120.

Constant amplitude output laser light pulse are produced with an intensity detector 164 that senses the intensity of the output laser light 120 and provides feedback to the flashlamp driver 162. Typically, the detector can be a diode or other photodetector that generates an intensity signal indicative of the amplitude of the output laser light. This signal is received by the flashlamp driver 162. There, the feedback signal is combined with the trigger signal. This allows the flashlamp driver to adaptively modify the level of the driving current to the flashlamps 124a, 124b in response to the instantaneous intensity of the output laser light. If the gain medium contains depleted dye, an increase in excitation is required to maintain constant output. If depleted dye can be removed quickly, the excitation pulse will remain nearly constant.

Usually, some exhausted dye solution tends to accumulate in the dye cell 105 over the course of the pulse. In fact, even with fast circulation, the percentage of new, unexhausted, dye is never as large as the moment before the flashlamps are first driven. At least some of the light generated in the dye cell 105 is absorbed by this exhausted dye solution and this effect tends to increase the threshold level of excitation needed for lasing. The intensity detector 164 detects any reduction in output light amplitude and causes the flashlamp to be driven harder to maintain constant output levels. Thus, the driving current is varied to maintain a constant amplitude in the output light amplitude. Alternatively, ramp trigger pulse can be used to generate an increasing or decreasing intensity in the output laser light, which is optimal for some applications.

Longer pulse durations are possible by circulating dye solution through the dye cell during the generation of the output laser light pulse while providing very intense exciting energies from the flashlamps 124a and 124b. The maximum obtainable pulse durations without replenishing depleted dye are approximately 2.5 msec. This is achieved by using special long-lived dyes. Using the same dyes in the present invention pulse durations of 5.0 msecs are achieved by replacing the dye solution in the dye cell 105 at least twice during the pulse. As a result, as the dye solution becomes partially or completely exhausted, new solution is added to the cell 105 to replace the old solution, which is pumped out by the circulator. In the present invention, the speed at which the dye is replaced in the dye cell 105 is dependent upon the how quickly the dye degrades. If the dye is exhausted after 2.5 msec, it must be replaced within that time. The total number of times that the dye is replaced in the dye cell 105 depends upon the required pulse duration. For example, a pulse duration of 10 msec, requires the equivalent of at least four dye replacements with dye lifetimes of 2.5 msec.

Photothermolysis treatment of larger ectatic vessels, for example, require the longer pulse durations obtainable by the present invention. Vessels of 100 and 200 micrometers in diameter have thermal relaxation times of 4.8 and 19.0 msec, respectively, and require similar pulse durations for optimally effective therapy. Energies are usually from 1 to 20 Joules, but fifty Joules can be required in hair removal applications.

FIG. 3 shows trigger signal voltage, the flashlamp excitation in Amperes, and the laser pulse amplitude 120 as a function of time during the pulse generation. Specifically, the controller 160 first engages the dye pump 150 to establish steady state dye flow through the dye cell 105 prior to the beginning of the laser pulse. The controller 160 then sends the trigger signal to the flashlamp driver 162. The length of this trigger signal defines the desired duration of the output laser light pulse 120. In the example shown, the duration is 5 milliseconds plus the latency time T that is required to excite the dye solution to lase.

Prior to the trigger signal, the flashlamp driver 162 maintains a slightly sub-operational current in the flashlamps 124a and 124b with a simmer current 205 as is conventional. Then, in response to the leading edge 206 of the trigger signal, the flashlamp driver 162 produces a driving current for the flashlamps 124a and 124b. The flashlamps, functioning as the laser-pumping devices, pump the dye solution in the dye cell 105 into an excited state causing it to lase when the fresh dye lasing threshold 208 is reached. This causes the output laser light pulse 120 having an amplitude indicated by reference numeral 212. Generally, the flashlamp driver 162 increases the current to the flashlamps 124a and 124b over the duration of the output laser pulse in response the feedback signal from the intensity detector 164. Progressively more driving current is required due to the accumulation of degraded dye solution in the cell 105 which yields an increasing lasing threshold 209. As some point, an equilibrium in the ratio of degraded dye to fresh dye is reached and the lasing threshold plateaues 211. Now, the excitation current is also steady state 210.

The resulting laser output 212 begins as the flashlamp power rises above the threshold level 208, time T after the rising edge of the trigger signal 206. The pulse terminates after five millisecond when the falling edge 215 of the trigger signal is generated by the controller 160.

Figure 4:
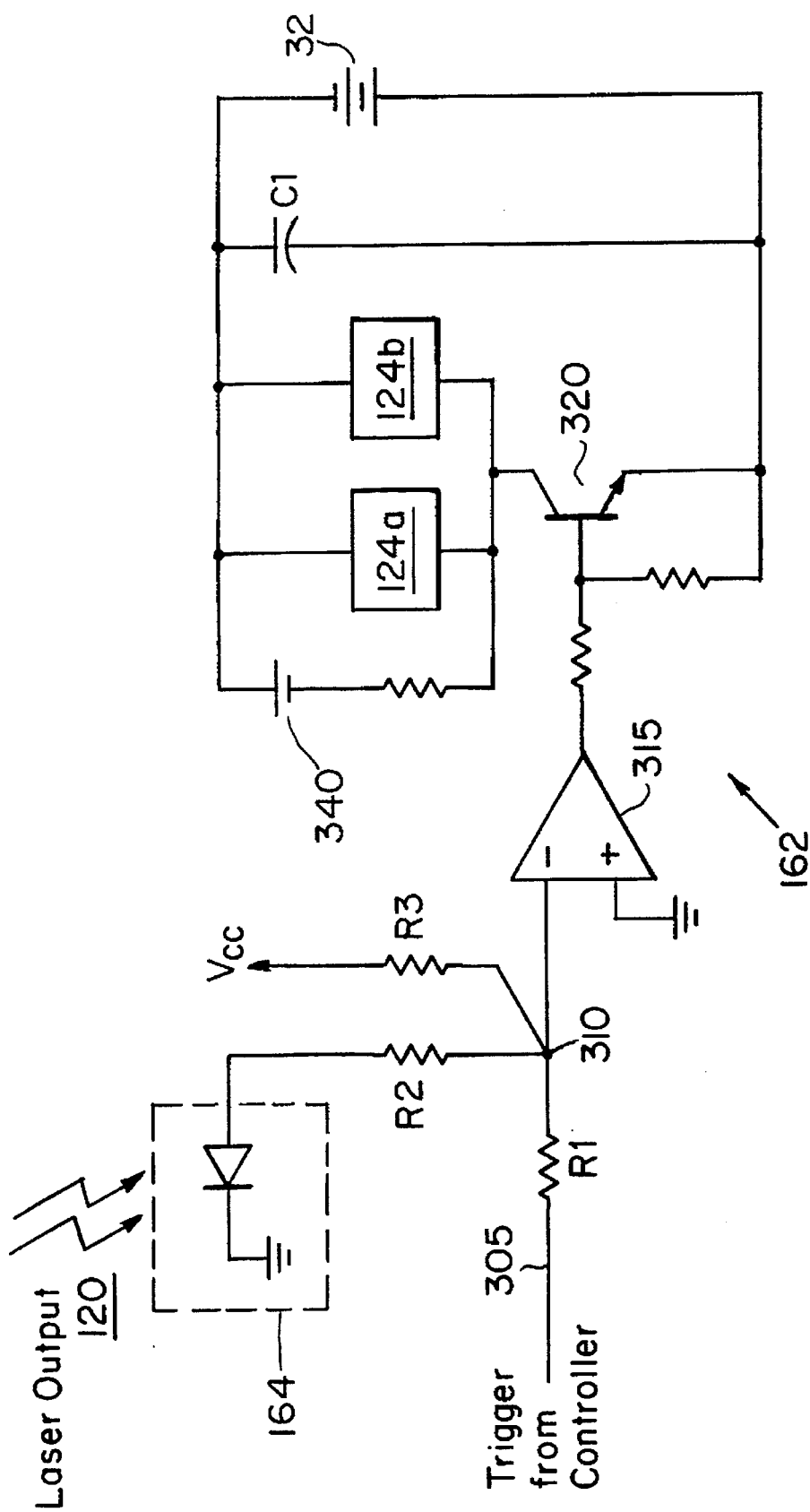
FIG. 4 is a circuit diagram of the flashlamp driver 162 of the present invention.

FIG. 4 is a circuit diagram of the flashlamp driver 162 shown in FIG. 2 that actively controls the level of driving of the flashlamps in response to the intensity of the generated laser light. Specifically, the flashlamp driver 162 receives the trigger signal from the controller 160 via conductor 305. This trigger signal defines the time for which the flashlamps will be driven and thus the duration of the laser light pulse. The length of the laser light pulse is tunable by changing the length of the trigger signal. This signal is received at a summing node 310 through a resistor R1. The feedback signal, which is indicative of the intensity of the output laser light 120, is received from the intensity detector 164 through a resistor R2 also at the summing node 310. The voltage of the summing node is biased by third resistor R3 that is connected between the summing node 310 and the supply voltage Vcc. In the particular embodiment shown, the trigger signal is a low level active signal which pulls the voltage of the summing node 310 below ground. A comparator 315 compares the voltage of the summing node to the ground potential. Thus, in response to a receipt of the trigger signal the comparator 315 turns a power transistor such as an insulated gate breakdown transistor (IGBT) or power Darlington 320 on, rendering the transistor conductive. This event places the voltage of a high voltage power supply 325 across the flashlamp, which generates a driving current to the flashlamps 124a and 124b. A capacitor C1 stores charge to assist in driving the flashlamps 124a, 124b. A simmer supply 340 is also connected across the flashlamps 124a and 124b to provide a simmer current to maintain a stable voltage across the lamp prior to the main excitation pulse. Without the simmer, operation is erratic. This simmer current is evident from portion 205 of the flashlamp excitation plot in FIG. 3.

The applicability of the flashlamp driver 162 is not limited to flashlamp-excited dye lasers with dye circulators but can be implemented as the driver for pumping devices that excite the gain media in many other types of lasers. Many types of lasers suffer from an increased excitation threshold across the length of a light pulse. Characteristically, conventional flashlamp-excited dye lasers, without dye flow suffer from this problem. This inventive pumping device driver 162 also find applicability to these lasers and also laser-excited dye lasers. In those cases, the flashlamp or other type of laser-pumping device will supply an ever increasing excitation current in response to any loss of intensity at the laser output.

Figure 5A:
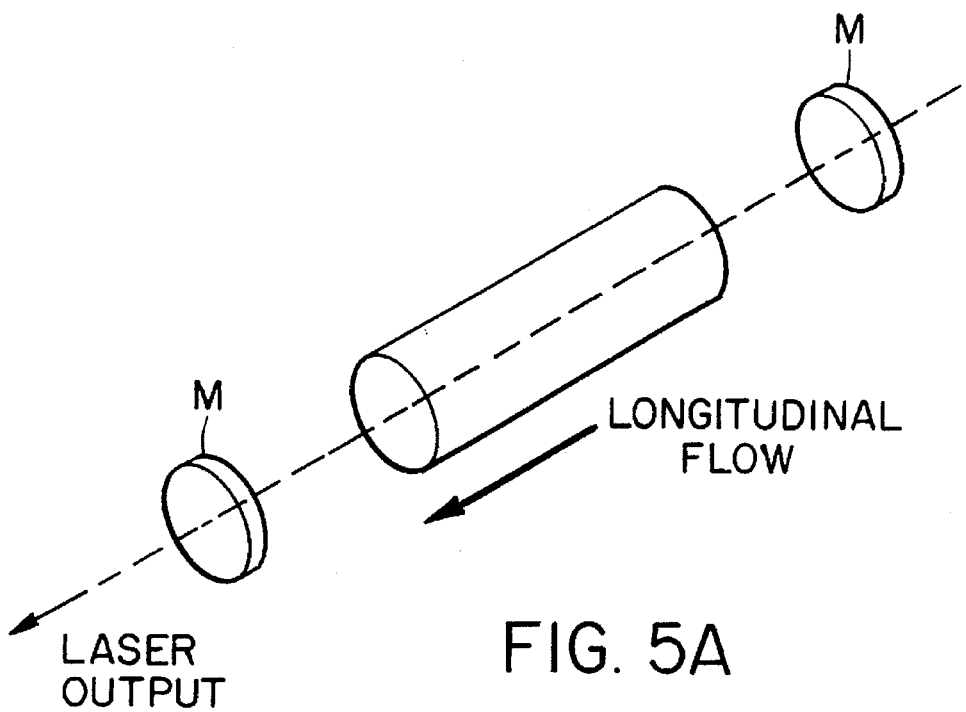
FIGS. 5A and 5B show the differences between longitudinal and transverse dye flow, respectively, through the resonant cavity of a laser.
Figure 5B:
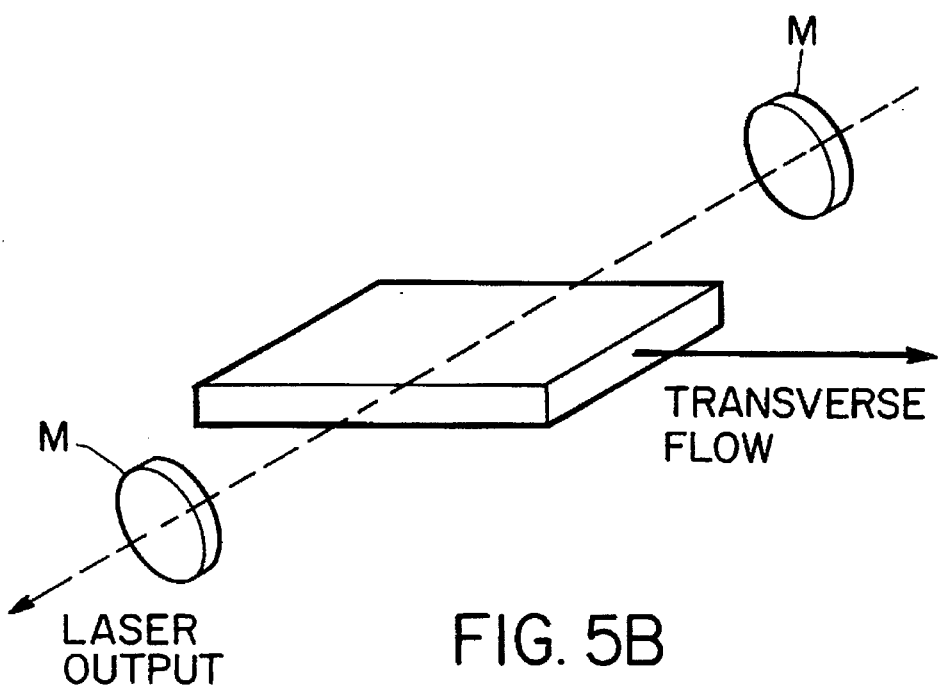

FIGS. 5A and 5B illustrate the key differences between a longitudinal flow dye laser and the transverse flow configuration. The first embodiment of FIG. 1 corresponds to the transverse flow type of FIG. 5B. These configurations generally provide shorter residence time of the dye solution in the dye cell 105. The dye solution must merely move across the width of the resonant cavity 110. The longitudinal flow configuration of FIG. 5A offers an alternative. But, since the dye solution moves along the length of the dye cell, resident time is longer for the same flow velocity.

Figure 6:
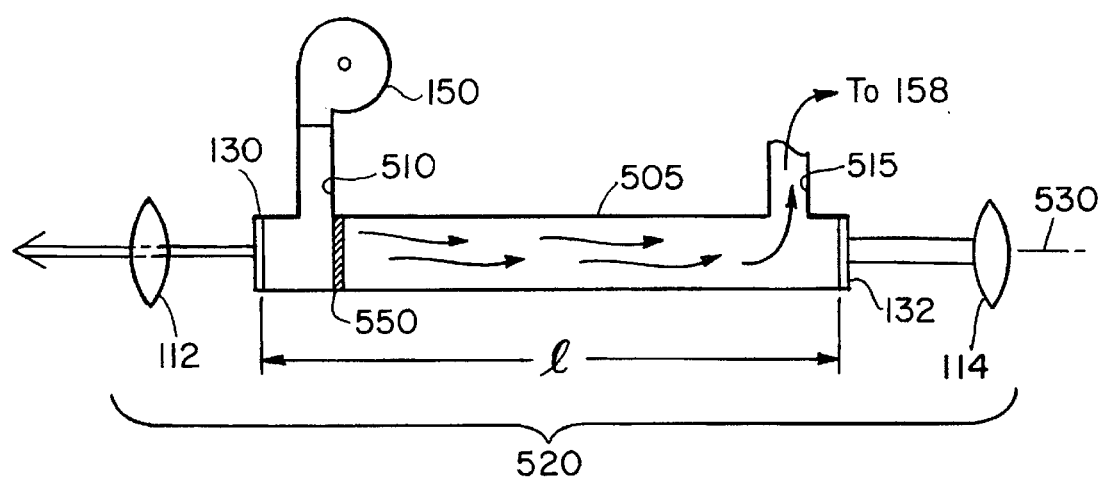
FIG. 6 schematically shows a dye cell 105 configured for longitudinal dye flow through the dye cell.

FIG. 6 illustrates a second embodiment of the dye cell 505 in which the dye solution travels longitudinally along the length of the dye cell 505, parallel to the laser axis 530. The dye solution is circulated through an input port 510 by a pump 150. The dye travels the length l of the dye cell 505 and exits an output port 515. First and second mirrors 112, 114 define the resonant cavity 520 in which the dye cell 505 is located as described in connection with FIG. 1.

The second embodiment configuration places certain limits on the dye cell 505 construction. A given cross-section of fluid 550 should traverse the length of the dye cell 505 in approximately 2.5 msec. This is a good estimate for the useable lifetime of dye solutions during lasing. But, velocity is limited by the pressure the dye cell 505 can withstand. A rule of thumb is that a flow of 10 meters per second is the maximum speed for pumps operating below 100 pound per square inch (psi). These factors limit the length of the dye cell 505 to approximately one inch in length.

Figure 7:
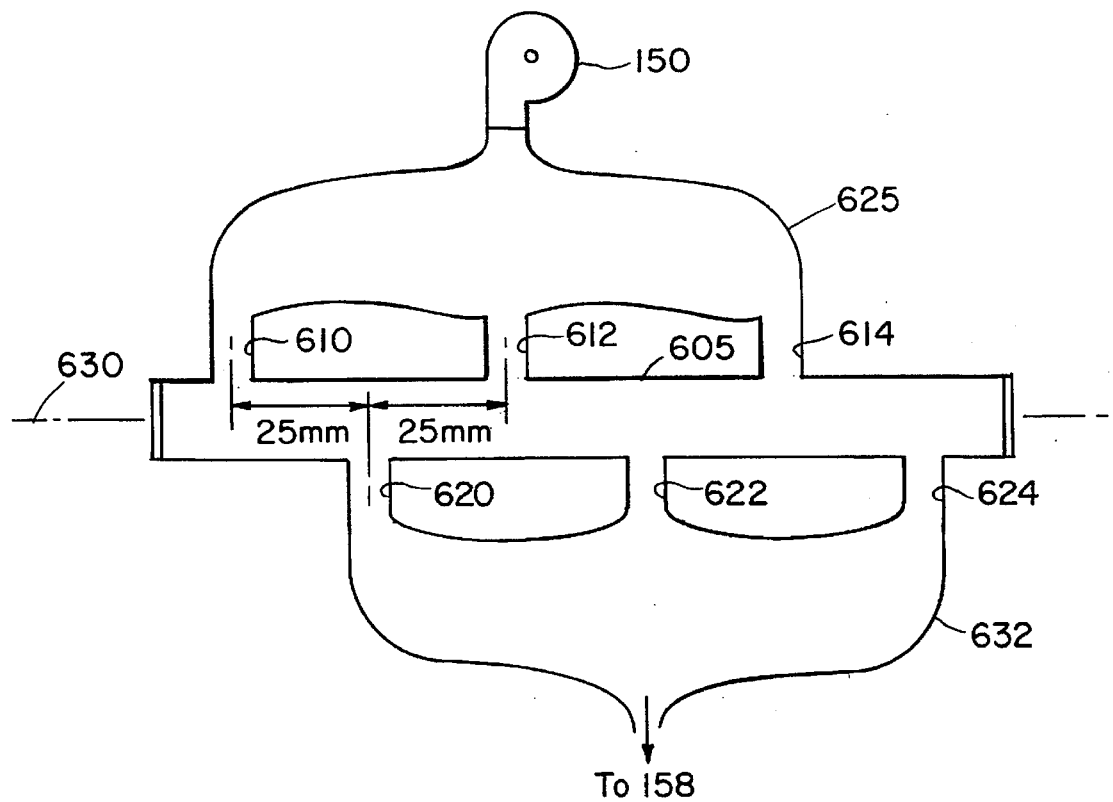
FIG. 7 schematically shows a dye cell 105 configured for longitudinal dye flow and having multiple input 610-614 and output ports 620-624 to reduce the residence time of dye solution in the dye cell 105.

FIG. 7 shows a third embodiment based upon a modification of the second embodiment of FIG. 6. Here, a plurality of dye input ports 610, 612, 614 are placed longitudinally along the length of dye cell 605. An input manifold 625 of the circulator supplies dye to each of these ports from a pump 650. Output ports 620, 622, 624 are placed between the input ports 610-614 on the opposite side of the dye cell 105. An output manifold 632 collects dye solution exiting the dye cell 605 through these ports. In this configuration, dye flowing through any one of the input ports 610-614 is divided and passes out both of the nearest output ports 620-624, again flowing parallel to the laser axis 630. If the longitudinal distance between an input port and the closest output port is approximately 25 mm, 50 mm between adjacent input ports, a flow velocity of 10 m/sec is sufficient to limit the residence time of the dye solution to 2.5 msec. This allows the dye solution to be interchanged twice in a 5 msec laser pulse duration or four times in a 10 msec pulse.

Dye Lasers having a transverse flow of dye gain media through the resonant cavity have been developed in the past in a number of different contexts for different applications. Continuous wave (cw) dye lasers have even been developed. The dye in these lasers is pumped by another laser. This laser is focused on a small spot on a curtain of the flowing dye solution. Thus, volume of dye excited in this device is very small. Only the small portion of the dye curtain in the path of the beam from the focused pumping laser is excited, and therefore generates light by stimulated emission. Even though this type of laser-excited dye laser generates a continuous wave output, it can not produce the kilowatts of average power required by medical applications.

Very high pulse rate transverse flow dye lasers have been developed for isotope separation applications. The intent of these designs is to produce output energies of approximately one Joule in a few microseconds. Thermal distortion, which limited firing rates were avoided by replacing the excited dye in the resonant cavity from a previous pulse with new dye and then triggering the flashlamp. Such devices have been shown to generate pulse frequencies of almost one kilohertz. In these industrial applications, the peak and average output powers and pulse frequencies far exceed those required for medical procedures where longer pulse durations, moderate peak and average powers at lower frequencies are preferred. Average power close to a kilowatt have been generated using transverse flow dye lasers. For medical application, average power of only a few Watts is required.

While this invention has been particularly shown and describe with references to preferred embodiments thereof, it will be understood by those skilled in the art that various changes in form and details may be made therein without departing from the spirit and scope of the invention as defined by the appended claims. For example, the resonator optical system could be integrated with the dye cell, making the cell coextensive with the resonant cavity.

I claim:

1. A method of operation for a flashlamp-excited pulse dye laser, the method comprising:

exciting original dye solution in a cavity with a flashlamp;

generating a laser light output pulse from the cavity with the excited original dye solution to at least partially exhaust the original dye solution;

replacing the at least partially exhausted original dye solution in the cavity with new dye solution at least once during a duration of the laser light output pulse;

exciting the new dye solution in the cavity during the duration of the laser light output pulse to extend the duration of the laser light output pulse beyond a time at which the original dye solution in the cavity would be exhausted and would quench the output laser light pulse if not replaced; and delivering the laser light output pulse to tissue of a patient.

2. A method as described in claim 1, further comprising replacing the dye solution to extend the duration of the output laser light pulse to at least five milliseconds.

3. A method as described in claim 1, further comprising generating the output laser light pulse with an energy of less than fifty Joules.

* * * * *